US008568450B2

(12) United States Patent
Stewart

(10) Patent No.: US 8,568,450 B2
(45) Date of Patent: Oct. 29, 2013

(54) ORAL ADMINISTRATION DEVICE

(75) Inventor: Bradley M. Stewart, Trevor, WI (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/368,724

(22) Filed: Feb. 8, 2012

(65) Prior Publication Data

US 2012/0143126 A1 Jun. 7, 2012

Related U.S. Application Data

(62) Division of application No. 11/385,177, filed on Mar. 21, 2006, now Pat. No. 8,118,773.

(51) Int. Cl.
*A61F 17/00* (2006.01)
*A61F 7/00* (2006.01)

(52) U.S. Cl.
USPC ................................ 606/234; 604/79; 604/77

(58) Field of Classification Search
USPC ...................................... 604/73–77; 606/234
See application file for complete search history.

(56) References Cited

U.S. PATENT DOCUMENTS 3,590,722 A 7/1971 Leptrone
3,892,243 A 7/1975 Bell
4,078,566 A * 3/1978 Urban, Jr. .................... 604/514
4,192,307 A 3/1980 Baer
D294,297 S 2/1988 Roehrig
5,078,734 A 1/1992 Noble
D326,151 S 5/1992 Wallace et al.
5,123,915 A 6/1992 Miller et al.
5,127,903 A 7/1992 Mailot et al.
5,176,705 A 1/1993 Noble
D335,187 S 4/1993 Stege
5,354,274 A 10/1994 Demeter et al.
5,363,890 A 11/1994 Yeung et al.
5,512,047 A 4/1996 Dvorak
5,514,142 A 5/1996 Dean-Homolka
5,601,605 A 2/1997 Crowe et al.
5,688,238 A * 11/1997 Moser et al. .................... 604/77
D391,642 S 3/1998 Fountain
5,728,137 A 3/1998 Anderson-Fignon
5,772,685 A 6/1998 Crowe et al.
5,827,527 A 10/1998 Leonard
D404,885 S 2/1999 Tomaszewski et al.
5,891,165 A 4/1999 Buckner
6,110,193 A * 8/2000 Chen ............................ 606/234
6,126,679 A 10/2000 Botts
6,197,044 B1 3/2001 Clayton
6,454,788 B1 9/2002 Ashton
6,482,225 B1 11/2002 Bingham et al.
D476,085 S 6/2003 Dumont et al.
6,575,999 B1 6/2003 Röhrig
6,588,613 B1 7/2003 Pechenik et al.
D492,417 S 6/2004 Davis (Continued)

FOREIGN PATENT DOCUMENTS

WO WO 03/051271 A1 6/2003

*Primary Examiner* — Nicholas Lucchesi
*Assistant Examiner* — Leah Stohr
(74) *Attorney, Agent, or Firm* — Lisa E. Winsor, Esq.

(57) ABSTRACT

An oral administration device having a nipple member and a frangible seal is disclosed. An oral administration system having a nipple member and a syringe to fill the nipple member is disclosed. An oral administration device having a vacuum package surrounding the oral administration device is also disclosed.

20 Claims, 3 Drawing Sheets

(56) References Cited

U.S. PATENT DOCUMENTS

| | | | |
|---|---|---|---|
| 6,752,824 | B2 | 6/2004 | Yancy |
| 6,776,157 | B2 | 8/2004 | Williams et al. |
| D501,256 | S | 1/2005 | Roehrig |
| 6,863,681 | B2 | 3/2005 | Dickerson |
| 2003/0034031 | A1 | 2/2003 | Lev et al. |
| 2004/0040556 | A1 | 3/2004 | Fillyaw |
| 2004/0178163 | A1 | 9/2004 | Kerns et al. |
| 2005/0125038 | A1 | 6/2005 | Inbar et al. |

* cited by examiner

ORAL ADMINISTRATION DEVICE

CROSS REFERENCE TO RELATED APPLICATIONS

This application is a Divisional Application which claims priority to U.S. patent application Ser. No. 11/385,177, filed on Mar. 21, 2006, now U.S. Pat. No. 8,118,773, the entire contents of which are incorporated herein by this reference.

FIELD OF THE INVENTION

This invention relates generally to oral administration devices, more particularly to an oral administration device for administering a variety of oral therapeutics including, but not limited to sweeteners, medicants, and vitamins to neonates or juveniles. Also, this invention relates to oral administration systems.

BACKGROUND OF RELATED ART

Administering oral therapeutics to juveniles, particularly neonates is problematic. Juveniles and neonates often squirm and are uncooperative when adults attempt to administer oral therapeutics. This can cause therapeutics to be spilled or wasted. Additionally, when a therapeutic is spilled or wasted it becomes difficult to determine the quantity of therapeutic that a juvenile or neonate has ingested. Moreover, when therapeutics that are to be administered in certain quantities are spilled before the juvenile or neonate ingests the therapeutic, a medical practitioner or parent may be unsure that the child has received the correct dose, making the treatment less effective.

Additionally, it is important that the device does not become contaminated when used multiple times. For example, when a practitioner gives sweetener to calm a neonate before a painful procedure, many practitioners dip the pacifier into a container of sweetener. This container generally becomes contaminated when the pacifier has to be dipped several time.

Some prior art administration devices require the practitioner to manipulate the package of the oral administration device in order to cover the administration device with a therapeutic. This manipulation can be tedious because the practitioner must make sure that enough therapeutic has coated the oral administration device. Moreover, this prior art device could be messy if the practitioner tries to coat the oral administration device more than one time. Another prior art method requires a practitioner to fill the oral administration device prior to administering to the neonate. This can be tedious if the therapeutic is spilled when poured into the device. These prior art methods also make it difficult to determine whether the juvenile or neonate received the correct dose of a particular therapeutic. Therefore, what is needed is an oral administration device where the therapeutic is contained in the oral administration device and force applied by the neonate's mouth will cause the sweetener to be expelled. Additionally, it would be beneficial to have an oral administration system that allows a practitioner to easily fill the device prior to administration.

SUMMARY

The present disclosure relates to an oral administration device for administering a variety of oral therapeutics including, but not limited to sweeteners, medicants, and vitamins to neonates or juveniles. The oral administration device comprises a nipple member for insertion into the juvenile's or neonate's mouth. In one embodiment, the nipple member has a frangible seal. Applied pressure causes the frangible seal to rupture allowing a therapeutic contained in the nipple member to escape. In another embodiment, the nipple member is surrounded by a vacuum package. The vacuum package prevents therapeutic contained in the nipple from leaking out of the nipple member prior to administration. The present invention also relates to an oral administration system that comprises an oral administration device including a nipple Patent member and a syringe. The syringe allows the oral administration device to be filled with a therapeutic prior to administration. Also, the present invention relates to a method of delivering a therapeutic using an oral administration device.

Additional features of the invention will become apparent to those skilled in the art upon consideration of the following detailed description of the preferred embodiments exemplified in the best mode of carrying out the invention as presently perceived.

DETAILED DESCRIPTION OF THE PREFERRED EMBODIMENTS

The present invention relates to an oral administration device for administering a variety of oral therapeutics including, but not limited to sweeteners, medicants, and vitamins to neonates or juveniles. With reference to the drawings, the oral administration device comprises a nipple member. In a preferred embodiment the nipple member includes a frangible seal. The frangible seal is manufactured to break when force is applied to the nipple member, preferably by the neonate or juvenile when sucking or chewing on the oral administration device. The ruptured frangible seal allows a therapeutic contained in the nipple to escape and enter the juvenile or patients mouth.

In another embodiment the nipple member is surrounded by a vacuum package. During the manufacturing process a vacuum is applied to the package surrounding at least the nipple member to create a sealed package that surrounds the oral administration device. The vacuum package prevents leakage of a therapeutic contained in the nipple and also keeps the nipple from becoming contaminated during the distribution process.

In yet another embodiment an oral administration system provides for an oral administration device having a nipple and a syringe to fill the nipple prior to administration.

Figure 1:
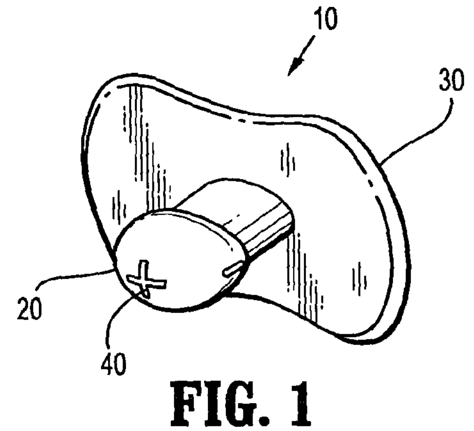
FIG. 1 is a perspective view of an oral administration device according to the present disclosure.
Figure 2:
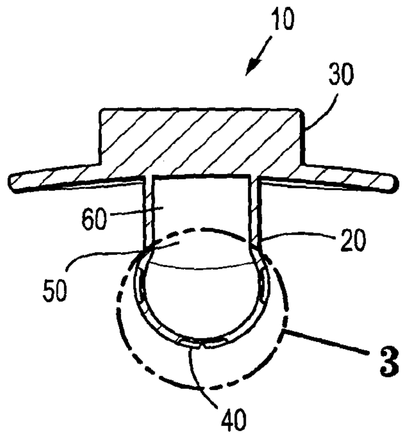
FIG. 2 is a plan view of an oral administration device according to the present disclosure.

With reference to the drawings, FIGS. 1-5 illustrate an oral administration device in accordance with the present disclosure. The oral administration device 10 comprises a nipple member 20. The nipple member 20 is connected to a base member 30. In FIG. 1 and FIG. 2 oral administration device 10 comprises nipple member 20 having a frangible seal 40. Nipple member 20 may be formed from any number of flexible materials known in the art including natural and synthetic polymers. Nipple member 20 may be formed from natural polymers including but not limited to natural rubbers, and polyisoprene. Also, nipple member 20 may be formed from a variety of thermoset, thermoplastic, or UV initiated polymers including but not limited to silicone, polyurethane, polyvinyl chloride, latex, and synthetic polyisoprene. Nipple member 20 is preferably formed from polyurethane and silicone. Nipple member 20 has a hollow section 50. Hollow section 50 can contain a therapeutic 60. Therapeutic 60 can include, but is not limited to sweeteners, medicants, and vitamins. Nipple 20 can be filled with therapeutic during the manufacturing process.

Figure 3:
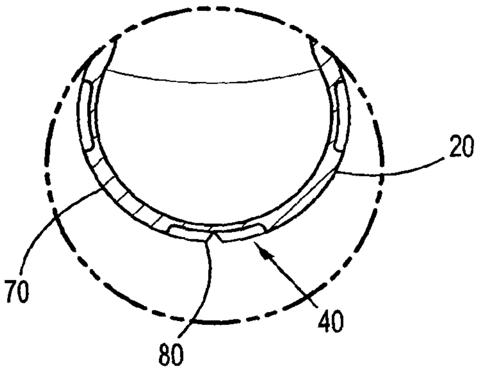
FIG. 3 is a partial enlarged view of the nipple member of an oral administration device
Figure 4:
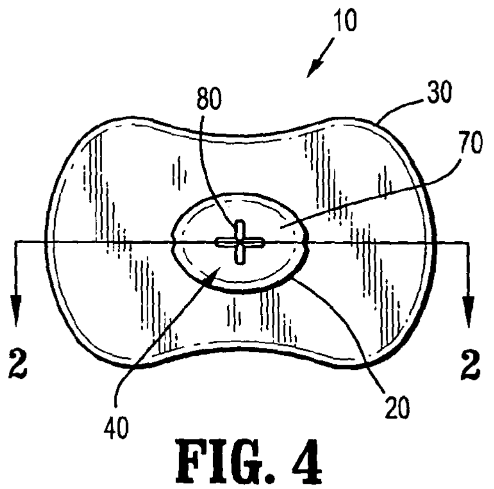
FIG. 4 is a plan view of the oral administration device according to the present disclosure.
Figure 5:
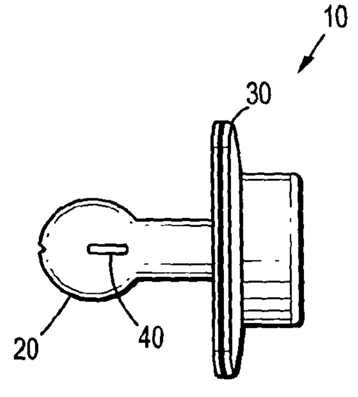
FIG. 5 is a plan view of an oral administration device according to the present disclosure.

Frangible seal 40 is shown in detail in FIG. 3 and FIG. 4. Frangible seal 40 is a seal which is intended to be broken, torn, or cut and which is thereby destroyed as a closure thereafter. Frangible seal 40 can be ruptured preferably by force created from the reflexive chewing or sucking action initiated by the neonate. Alternatively, frangible seal 40 can be ruptured by piercing frangible seal 40 with a sharp object. Frangible seal 40 prevents the therapeutic 60 from leaking out of the nipple member during distribution prior to administration. The tip 70 of nipple member 20 is shown in FIG. 3 and FIG. 4. In FIG. 3 and FIG. 4, tip 70 includes the nipple member 20 molded with frangible seal 40. Frangible seal 40 is an area of the nipple member molded to be thinner than the remaining area of nipple member 20. Thinner area 80 allows for the nipple to be easily ruptured with pressure or through piercing. In FIG. 4, thinner area 80 is a cross shaped slit. Alternatively, frangible seal 40 could be in the shape of a horizontal slit, vertical slit, oval, circular, or any variety thereof. As shown in FIG. 5, frangible seal 40 can be located anywhere on the nipple member that assists in administering therapeutic 60. Additionally, nipple member 20 can have multiple frangible seals.

When therapeutic 60 contained in nipple member 20 comprises a sweetener, the sweetener can be formulated from a wide variety of pharmaceutically acceptable or food acceptable components. Possible sweeteners include, but are not limited to, sucrose or fructose. Sweeteners can also include both caloric and/or noncaloric sweeteners. Medicants or vitamins can also be administered according to the present invention. Therapeutic 60 can be combined with starches, gums, gelatins and the like to provide a sufficient therapeutic composition for oral administration in accordance with the present invention.

Figure 6:
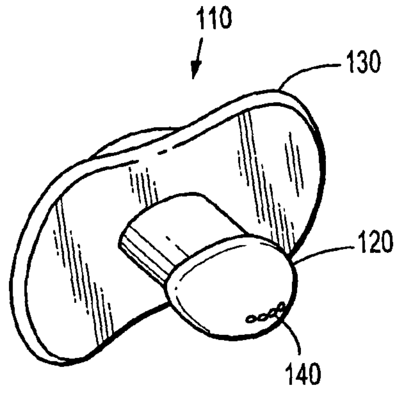
FIG. 6 is perspective view of another embodiment of an oral administration device according to the present disclosure.
Figure 7:
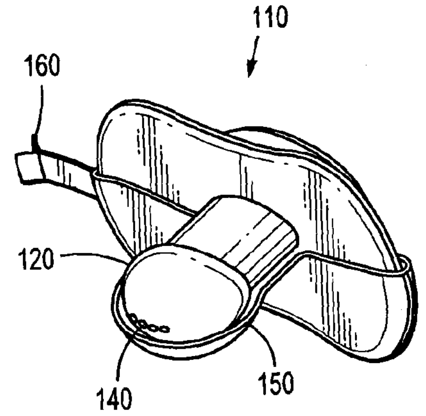
FIG. 7 is a perspective view of another embodiment according to the present invention including a vacuum package.
Figure 8:
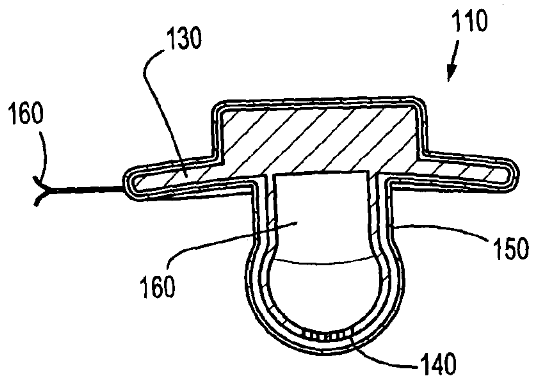
FIG. 8 is a plan view of another embodiment according to the present invention including a vacuum package.

FIG. 6, FIG. 7, and FIG. 8 illustrate an alternative embodiment of the oral administration device of the present disclosure. FIG. 6 depicts oral administration device 110 prior to packaging processes. Oral administration device 110 has nipple member 120 connected to base 130. Nipple member 120 has pierced holes 140. Pierced holes 140 can be in a variety of patterns and shapes. Additionally, pierced holes 140 can be a single hole. Nipple member 120 can alternatively be molded with a frangible seal. The vacuum packaging 150 surrounding oral administration device 110 is shown in FIG. 7 and FIG. 8. Vacuum packaging can be accomplished in a variety of ways well know in the art. Preferably, during manufacturing, two pieces of vacuum packaging acceptable material are placed over the oral administration device. The two pieces of material are sealed together. As shown in FIG. 8 a vacuum is applied to the package and the two pieces tightly surround the oral administration device 110 to prevent therapeutic 160 from leaking from nipple member 120. An adult can remove vacuum package 150 by pulling or tearing vacuum package 150 before use. Preferably, vacuum package 150 will include a tab 160 to remove vacuum package 150. The packaging material of vacuum package 150 can be any sealable material. The packaging material of vacuum package 150 is preferably polyethylene.

Figure 9:
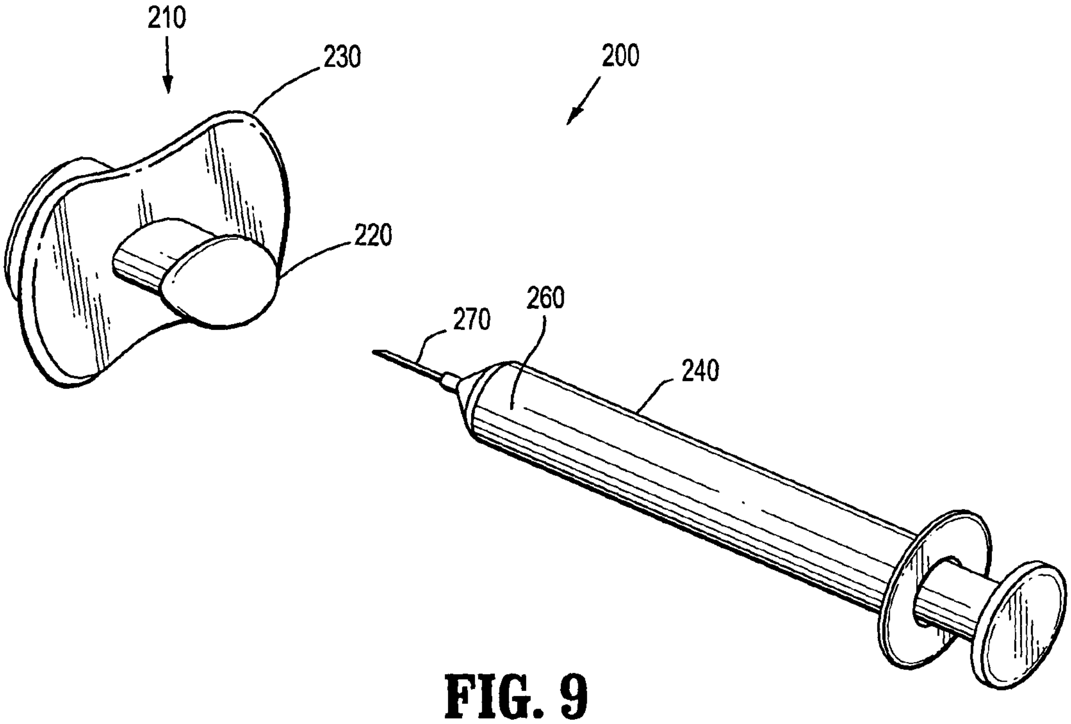
FIG. 9 is a perspective view of another embodiment including a syringe.
Figure 10:
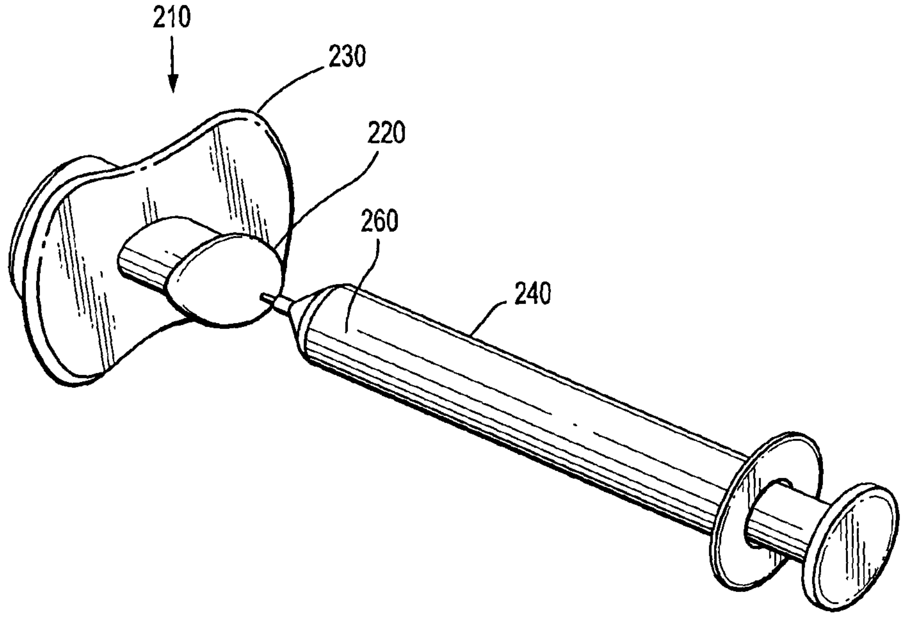
FIG. 10 is a perspective view of another embodiment including a syringe.

Another embodiment is shown in FIGS. 9 and 10. FIG. 9 and FIG. 10 illustrate an oral administration system 200. Oral administration system 200 comprises an oral administration device 210 having a nipple member 220. Nipple member 220 is connected to base 230. Oral administration system 200 also has a syringe 240. Syringe 240 includes needle 270. Syringe 240 can be a variety of syringes, needles, and combinations thereof such as MONOJECT needles and syringes available from Tyco Healthcare Group LP. Syringe 240 is filled with therapeutic 260. Therapeutic 260 can include, but is not limited to, sweeteners, medicants, and vitamins. During manufacturing syringe 240 is filled with therapeutic 260. Alternatively, syringe 240 can be filled by an adult after prior to administration. As shown by FIG. 10, syringe 240 pierces nipple member 220. Alternatively, base member 230 can be constructed to allow oral administration device 210 to be filled through base member 230. An adult can fill the syringe with an appropriate amount of therapeutic 260. The oral administration device 210 is given to an infant or neonate for administration of therapeutic 260.

Preferably, syringe 240 is equipped with a large gauge needle such as a 16 or 18 gauge needle. Syringe 240 can be used to pierce nipple member 220 one or more times to provide a sufficient passageway for administration of therapeutic 260.

In light of the foregoing disclosure of the invention and description of the preferred embodiments, those skilled in this area of technology will readily understand that various modifications and adaptations can be made without departing from the scope and spirit of the invention.

I claim:

1. An oral administration system comprising:

a nipple member including a frangible seal that ruptures upon being subjected to a predetermined suction force when in a patient's mouth; and a syringe including at least one substance, the syringe configured to at least partially fill the nipple member with the at least one substance prior to administration of the nipple member, the frangible seal retaining the at least one substance within the nipple member prior to a rupturing of the frangible seal, the nipple member enabling the at least one substance to freely dispense from the nipple member upon a rupturing of the frangible seal.

2. The system of claim 1, wherein the nipple member is attached to a base member.

3. The system of claim 2, wherein the base member is attached to a handle.

4. The system of claim 2, wherein the nipple member includes an outer wall having a bulbous surface, the outer wall exposed to the interior of the patient's mouth upon at least partial positioning therein, the bulbous surface having the frangible seal defined therein, the frangible seal extending partially along the bulbous surface.

5. The system of claim 4, wherein the frangible seal includes a wall segment having a cross-sectional thickness which is less than the cross-sectional thickness of wall segments adjacent the frangible seal.

6. The system of claim 4, wherein the frangible seal includes at least one of a: horizontal slit, vertical slit, oval slit, circular slit, and combinations thereof.

7. The oral administration device of claim 1, wherein the frangible seal is incapable of closure upon the rupturing of the frangible seal.

8. The system of claim 1, wherein the at least one substance includes a sweetener.

9. The system of claim 8, wherein the sweetener is selected from the group consisting of sucrose, fructose, and mixtures of caloric and/or noncaloric sweeteners.

10. The system of claim 1, wherein the at least one substance includes a medicant.

11. The system of claim 1, wherein the at least one substance includes a vitamin.

12. The system of claim 1, wherein the nipple member includes a flexible material.

13. The system of claim 12, wherein the flexible material is a natural polymer.

14. The system of claim 12, wherein the flexible material is a synthetic polymer.

15. The system of claim 14, wherein the synthetic polymer is polyurethane.

16. The system of claim 14, wherein the synthetic polymer is silicone.

17. An oral administration system comprising:

a syringe;

a base member; and a nipple member extending from the base member, the nipple member including an outer wall having a bulbous surface and being configured and dimensioned for at least partial positioning in a patient's mouth, the bulbous surface defining a frangible seal that extends partially therealong, the frangible seal being exposed to the interior of the patient's mouth upon positioning of the nipple member therein, the frangible seal being configured and dimensioned to at least partially rupture when subjected to a predetermined suction force during administration in the patient's mouth.

18. The oral administration device of claim 17, wherein the frangible seal is incapable of closure upon the rupturing of the frangible seal.

19. An oral administration system comprising:

a base member;

a nipple member extending from the base member, the nipple member including an outer wall having a bulbous surface and being dimensioned for at least partial positioning in a patient's mouth, the bulbous surface defining a frangible seal that extends along a portion of the bulbous surface, the frangible seal being disposed external of the base member and dimensioned and adapted to be exposed to the interior of the patient's mouth upon at least partial positioning of the frangible seal in the patient's mouth, the frangible seal being configured and dimensioned to at least partially rupture when subjected to a predetermined force during administration in the patient's mouth; and at least one substance configured and dimensioned to be positioned within the nipple member via a syringe prior to administration of the nipple member in the patient's mouth, the at least one substance configured and dimensioned to emerge from the nipple member upon the at least partial rupture of the frangible seal.

20. The system of claim 19, wherein the at least one substance includes a therapeutic agent.

* * * * *